(12) United States Patent
Hauge et al.

(10) Patent No.: US 8,170,639 B2
(45) Date of Patent: May 1, 2012

(54) CASE FOR DEFIBRILLATOR ELECTRODE PADS AND RELEASE LINER

(75) Inventors: Patrick L. Hauge, Bellevue, WA (US); Daniel J. Powers, Issaquah, WA (US); Eric Jonsen, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 207 days.

(21) Appl. No.: 12/513,688

(22) PCT Filed: Nov. 6, 2007

(86) PCT No.: PCT/IB2007/054499
§ 371 (c)(1),
(2), (4) Date: Apr. 16, 2010

(87) PCT Pub. No.: WO2008/059396
PCT Pub. Date: May 22, 2008

(65) Prior Publication Data
US 2010/0228332 A1    Sep. 9, 2010

Related U.S. Application Data

(60) Provisional application No. 60/865,486, filed on Nov. 13, 2006.

(30) Foreign Application Priority Data

Nov. 6, 2007  (WO) ................. PCT/IB2007/054499

(51) Int. Cl.
*A61B 5/04* (2006.01)
(52) U.S. Cl. ....................................................... 600/392
(58) Field of Classification Search .................. 600/392, 600/395, 391, 386; 607/5, 96, 36, 142, 152
See application file for complete search history.

(56) References Cited

U.S. PATENT DOCUMENTS

| 2002/0117408 A1* | 8/2002 | Solosko et al. ............... 206/210 |
| 2003/0055478 A1 | 3/2003 | Lyster et al. |
| 2003/0092978 A1* | 5/2003 | Fisher, III ..................... 600/391 |

FOREIGN PATENT DOCUMENTS

| WO | 2005/092430 A | 10/2005 |
| WO | 2006046160 A | 5/2006 |

\* cited by examiner

*Primary Examiner* — George Manuel
*Assistant Examiner* — Robert Wieland
(74) *Attorney, Agent, or Firm* — W. Brinton Yorks, Jr.

(57) ABSTRACT

A case for defibrillator electrode pads on a release liner is described which protects the pads prior to use and retains them in either an electrically connected or electrically disconnected configuration. When the case is closed, spring contacts on opposite sides of the inside of the case retain the pads and release liner in place. The retention either holds electrical conductors in contact with each other to retain the pads in electrical connection with each other, or in a different configuration in which the pads are not electrically connected.

18 Claims, 8 Drawing Sheets

CASE FOR DEFIBRILLATOR ELECTRODE PADS AND RELEASE LINER

This invention relates to defibrillators for cardiac resuscitation and, in particular, to electrode pads for defibrillators.

Cardiac arrest is a life-threatening medical condition in which the patient's heart fails to provide blood flow to support life. A defibrillator can be used to deliver defibrillating shocks to a patient suffering from cardiac arrest. The defibrillator resolves this condition by delivering a high-voltage impulse to the heart in order to restore normal rhythm and contractile function in patients who are experiencing arrhythmia such as VF (ventricular fibrillation) or VT (ventricular tachycardia) that is not accompanied by spontaneous circulation. There are several classes of defibrillators, including manual defibrillators, implantable defibrillators, and automatic external defibrillators (AEDs). AEDs differ from manual defibrillators in that AEDs can automatically analyze the electrocardiogram (ECG) rhythm to determine if defibrillation is necessary. The defibrillator analyzes the ECG signal for signs of arrhythmia. If VF is detected, the defibrillator signals the rescuer that a shock is advised. After the detection of VF or other shockable rhythm, the rescuer presses a shock button on the defibrillator to deliver a defibrillation pulse to resuscitate the patient.

External defibrillators act through electrode pads applied across the chest of the patient. The electrodes adhesively attach to the patient and are used both to acquire an ECG signal from the patient's heart and to apply the defibrillating shock. AED electrodes commonly are formed by locating a foil or metallized electrode between a flexible nonconductive backing and a conductive adhesive gel. The conductive adhesive attaches the electrode securely to the patient. Gels, however, will dry out (desiccate) over time and have a finite shelf life. A typical shelf life for an electrode with gel adhesive is about two years, after which the electrodes must be replaced. Some AEDs use electrodes which are simply replaced when the safe shelf life period has expired. Other AEDs have an internal self-test circuit which periodically tests the electrodes and detects desiccation by an impedance change. For self-test electrodes the electrodes are electrically connected to each other to form a continuous closed loop circuit that is tested. The closed loop circuit is broken when the electrode pads are deployed for use.

In the case of both self-tested electrodes and non-self-tested electrodes, it is typical that the electrodes will be connected to the AED while stored prior to use so that the rescuer does not need to connect them; they are already pre-connected and ready for use. The self-test electrodes are pre-connected with the loop circuit closed for self-testing. The non-self-test electrodes are generally not connected in a closed loop circuit while stored prior to use. Hence, two different styles of electrodes are needed for self-testing and non-self-testing defibrillators.

Our concurrently filed U.S. patent application 60/865,482 describes a release liner for a pair of electrodes with a moisture-impermeable surface on which the electrodes are peripherally attached, sealing the conductive gel of the electrodes between the moisture-impermeable backing of the electrodes and the moisture-impermeable surface of the release liner. The release liner also has an electrical contact electrically connected to each electrode. When the release liner is folded in a first configuration the electrical contacts are brought into contact with each other, completing an electrical connection between the two electrodes. When the release liner is not in this configuration there is no electrical connection between the two electrodes. It would be desirable to have a device which both retains the release liner and electrodes in the desired configuration and protects the release liner and electrodes prior to use.

In accordance with the principles of the present invention, a release liner for defibrillator electrode pads is described which can be used for electrode pads connected in a closed loop for self-test and for electrode pads connected in an open circuit. The release liner includes two areas where electrode pads are attached prior to use. When the electrodes are attached to the release liner the adhesive gel of each electrode is electrically connected to a conductor that provides the closed circuit for self-test electrodes. When the release liner is folded one way a closed circuit is completed between the electrodes. When not folded this way there is no closed circuit between the electrodes. In one embodiment described below a clip is provided to retain the folded release liner in either the closed circuit or open circuit configuration. In another embodiment a case is provided with an internal clip that retains the release liner and electrodes in the desired configuration. The case also protects the electrodes prior to use.

In the drawings:

FIG. 5a is a perspective view of a case for a release liner and electrode of the present invention and FIG. 5b is a cross-sectional view of the case of FIG. 5a.

Figure 1:
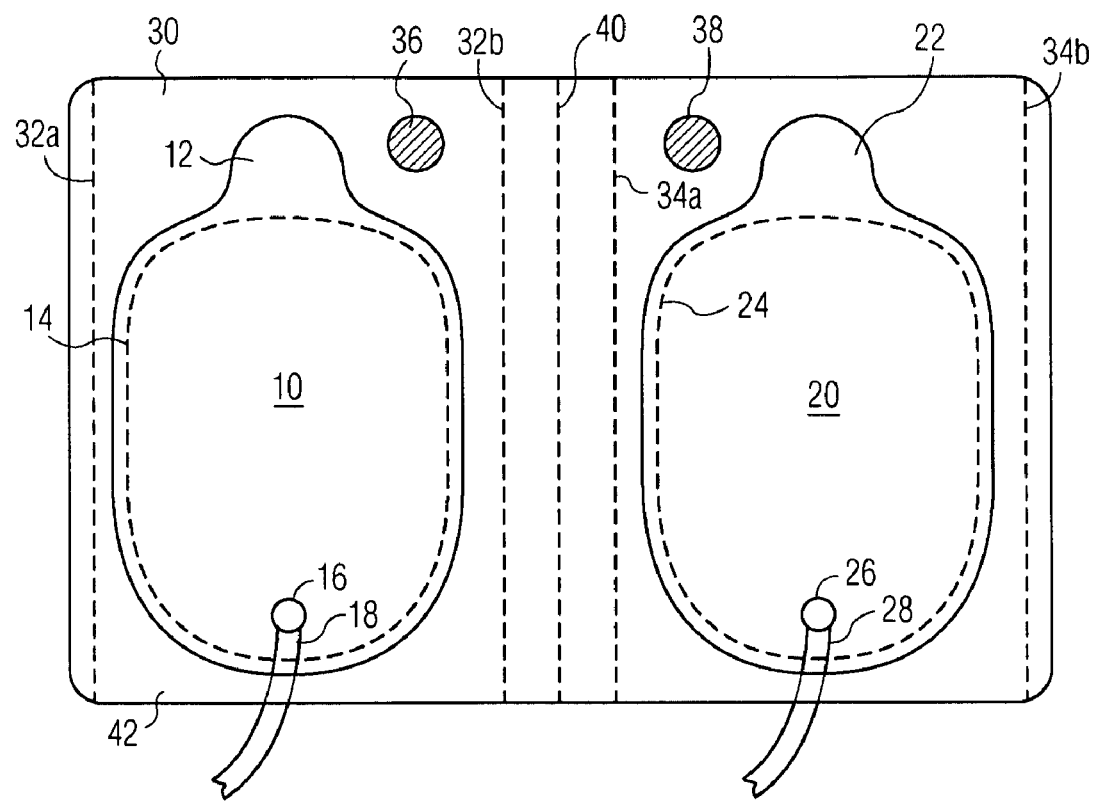
FIG. 1 illustrates a halibut-style release liner and electrodes constructed in accordance with the principles of the present invention.

Referring first to FIG. 1, a halibut-style release liner 30 and electrode set 10,20 is shown in plan view. The style is referred to as halibut-style herein by reason of the resemblance of the relatively flat, flexible electrodes 10,20 to the fish of the same name when attached to the release liner. In this view the nonconductive backing surface of the electrodes 10,20 is facing the viewer. The adhesive gel on the other side is in contact with the release surface 42 of the release liner 30. A wire 18,28 is connected through the backing of each electrode 10,20 to the inner conductive layer of the electrode and is held in place by a fastener such as a rivet 16,26. Desiccation of the gel is retarded by sealing the nonconductive backing of each electrode to the moisture impermeable release surface 42 of the release liner. The seals 14, 24 are made around the periphery of the gel areas of the electrodes. A tab 12, 22 is formed at the end of the backing of the electrodes and may be grasped by a user to pull the electrodes away from the release liner when they are to be used.

Located inside the release liner 30 under each electrode 10,20 is a conductive sheet 44 (see FIG. 2) of metallic foil or other thin conductive material. The lateral extent of each sheet is indicated by dashed lines 32a,32b and 34a,34b. A hole 36, 38 is formed in the outer release surface layer 42 to give access to each conductive sheet. It is seen that each side of the halibut release liner of FIG. 1 is a mirror image of the other about the center fold line 40 of the release liner 30. In accordance with the principles of the present invention, when the two sides are folded up and toward each other, the hole 36 will be opposite the hole 38 so that the conductive sheets visible through the holes can be brought into electrical contact with each other. When the release liner remains flat as shown in the drawing or when folded back along the fold line 40 so that the back sides (not visible in FIG. 1) are brought into contact with each other, there is no contact or electrical connection of the sheets within the release liner.

Figure 2A:
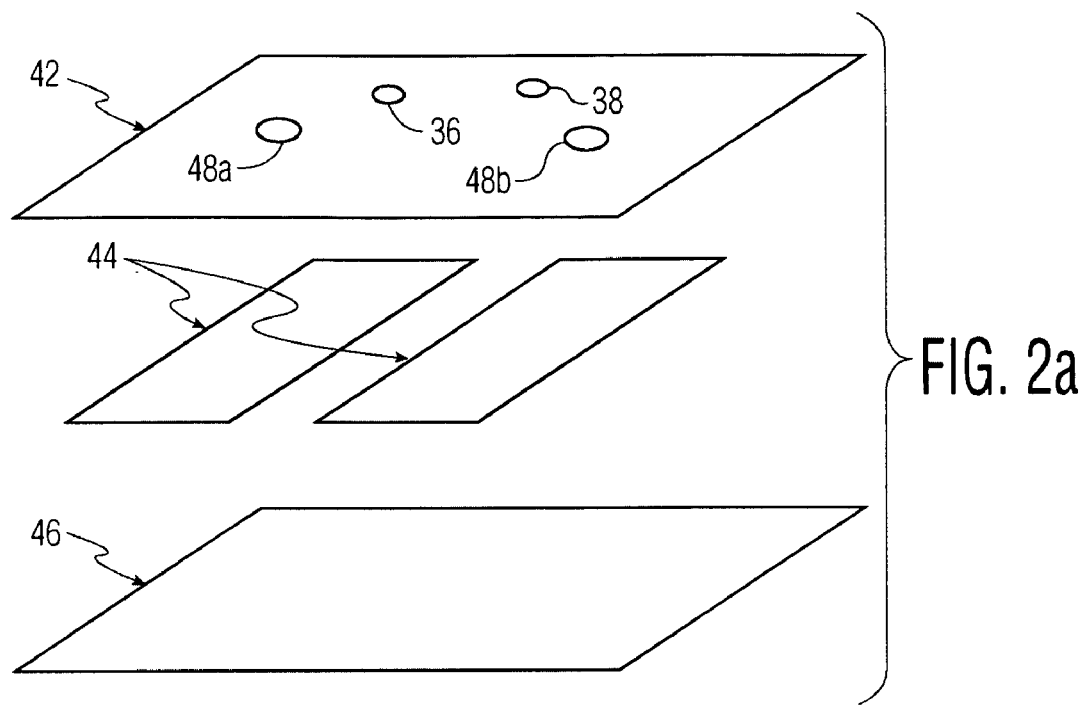
FIG. 2a illustrates a first example of a release liner of the present invention in an exploded view.
Figure 2B:
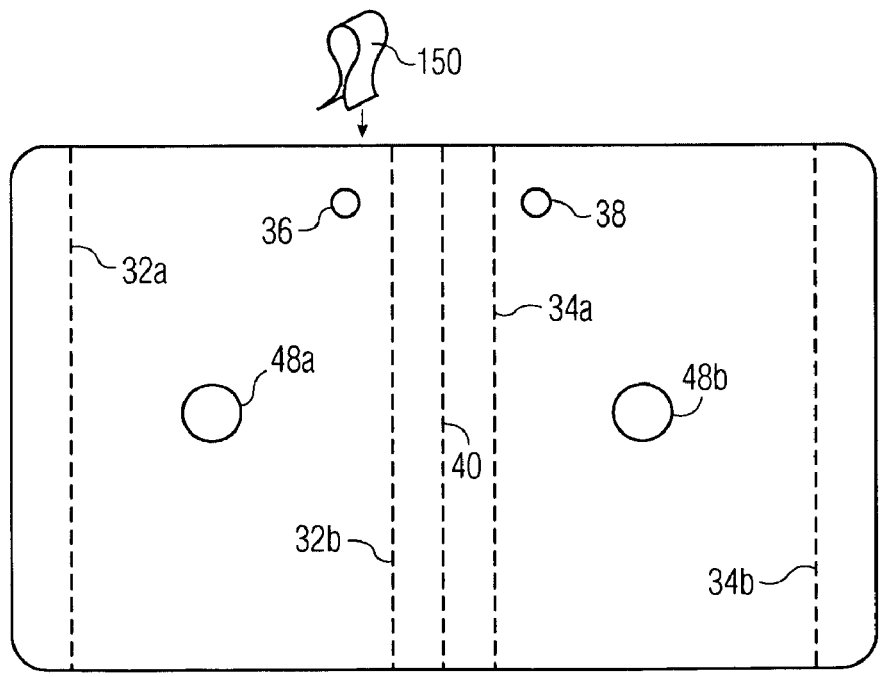
FIG. 2b is a plan view of the release liner of FIG. 2a after assembly.

FIGS. 2a and 2b illustrate how the manner in which the release liner is folded dictates whether an open circuit or closed circuit is formed with the electrodes. In the exploded view of FIG. 2a, the nonconductive release surface layer 42 is seen to have four holes in it, the two previously described access holes 36,38 for the inner conductive sheets 44 and two holes 48a and 48b which underlie the electrodes when they are sealed to the layer 42.

The bottom layer of the release liner is a nonconductive layer 46. Between the layers 42 and 46 are the two conductive sheets 44 which underlie the electrode positions and holes 36,38 on each side of the release liner. When the conductive sheets are sealed between layers 42 and 46 their lateral sides in this example are positioned as shown by dashed lines 32a,32b for the left side conductive sheet and dashed lines 34a,34b for the right side conductive sheet as shown in FIG. 2b. Referring to FIG. 1 and FIG. 2b, it is apparent how the electrodes 10,20 can be electrically connected together. When the release liner is folded along fold line 40 so that the left and right upper sides are brought into contact with each other, an electrical circuit is completed between the wire 18 of the left electrode 10, the conductive layer of that electrode, its gel layer which is in contact with the left conductive sheet 44 of the release liner through the hole 48a, through holes 36 and 38 and the contact between the left and right conductive sheets 44 through those holes, from the right conductive sheet to the gel of the right electrode 20 through hole 48b, to the conductive layer of the electrode 20 and to its wire 28. When the two wires 18,28 are connected to a defibrillator a closed loop circuit is thus formed with the defibrillator. To keep the left and right conductive sheets 44 in electrical contact with each other when the release liner is folded closed in this configuration, a clip 150 or other fastening device may be applied to pinch the two conductive sheets 44 into contact with each other through holes 36 and 38 as shown in FIG. 2b. Other alternative holding techniques may be used such as fastening the sheets with a conductive adhesive when holes 36 and 38 are brought into contact with each other. In this closed loop circuit configuration the electrodes may be readily self-tested by signals applied by the defibrillator to which wires 18 and 28 are connected.

When the release liner and electrode are to be connected to a defibrillator which does not require closed loop connection of the electrodes it is sufficient that the conductive sheets visible through the holes 36 and 38 not be brought into contact with each other. The release liner can be folded the opposite way with the back sides of the release liner (layer 46) in contact with each other. If desired the clip 150 can be used to retain the release liner in this folded configuration. The release liner can alternatively be left unfolded as it is in FIGS. 1 and 2b.

Variations of this example will be readily apparent to those skilled in the art. For instance the conductive sheets 44 do not need to have the shape illustrated in this example; they can simply be conductors between the electrode hole 48a and the access hole 36 and between electrode hole 48b and access hole 38. One of the electrodes could be located on the other side (the layer 46 side) of the release liner provided that the electrode hole for that electrode were on that side of the release liner. The holes 36,38 could be punched through the release layer 42 but the punched material not removed unless the closed loop configuration were to be employed. Separate insulating covers could be used over one or both of the holes 36,38 to prevent electrical connection between the two conductive sheets 44 even in the forward folded condition. Other variations are also possible.

Figure 3:
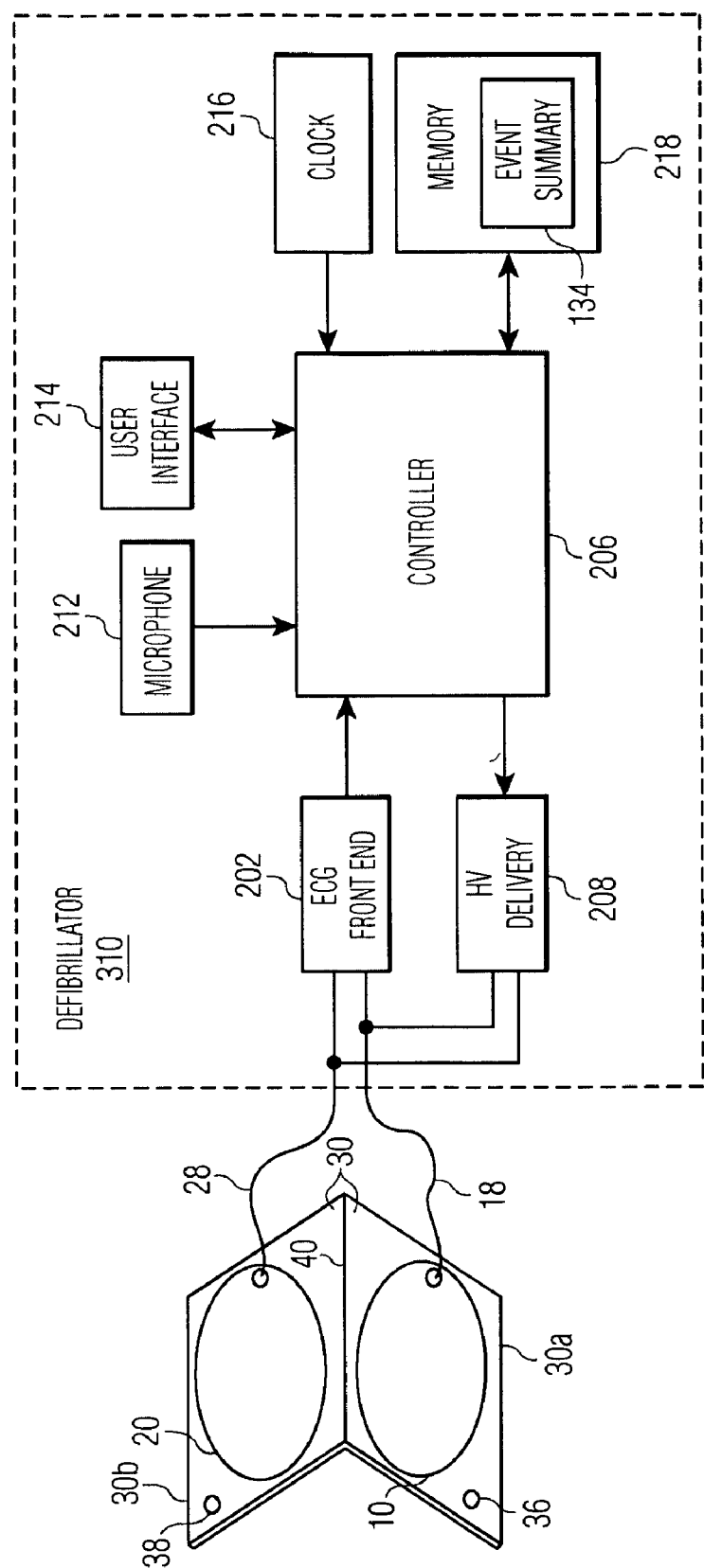
FIG. 3 illustrates a halibut-style release liner and electrodes connected to a defibrillator.

FIG. 3 shows the halibut release liner and electrodes when connected to a defibrillator 310. An ECG front end circuit 202 is connected to the wires 18,28 of the electrodes 10,20. In FIG. 3 the electrodes 10,20 are shown peripherally attached to the two sides 30a,30b of the release liner 30 prior to being peeled off of the release liner and attached to the patient. The ECG front end circuit 202 operates to amplify, buffer, filter and digitize an electrical ECG signal generated by the patient's heart and picked up by the electrodes to produce a stream of digitized ECG samples. The digitized ECG samples are provided to a controller 206 that performs an analysis to detect VF, shockable VT or other shockable rhythm. If a shockable rhythm is detected, the controller 206 sends a signal to HV (high voltage) delivery circuit 208 to charge a high voltage capacitor of circuit 208 in preparation for delivering a shock, and a shock button on a user interface 214 is activated to begin flashing. The rescuer 220 is then advised by an audible instruction to keep away from the patient ("hands off" instruction). When the rescuer presses the shock button on the user interface 214 a defibrillation shock is delivered from the HV delivery circuit 208 to the patient through the electrodes 10,20.

The controller 206 is coupled to further receive input from a microphone 212 to produce a voice strip. The analog audio signal from the microphone 212 is preferably digitized to produce a stream of digitized audio samples which may be stored as part of an event summary 134 in a memory 218. The user interface 214 may consist of a display, an audio speaker, and control buttons such as an on-off button and a shock button for providing user control as well as visual and audible prompts. A user interface of the present invention may also include one or more control buttons for selecting a rescue protocol stored in memory 218 to be carried out during a rescue. A clock 216 provides real-time or elapsed time clock data to the controller 206 for time-stamping information contained in the event summary 134. The memory 218, implemented either as on-board RAM, a removable memory card, or a combination of different memory technologies, operates to store the event summary 134 digitally as it is compiled during the treatment of the patient 210. The event summary 134 may include the streams of digitized ECG, audio samples, and other event data as previously described.

Figure 4:
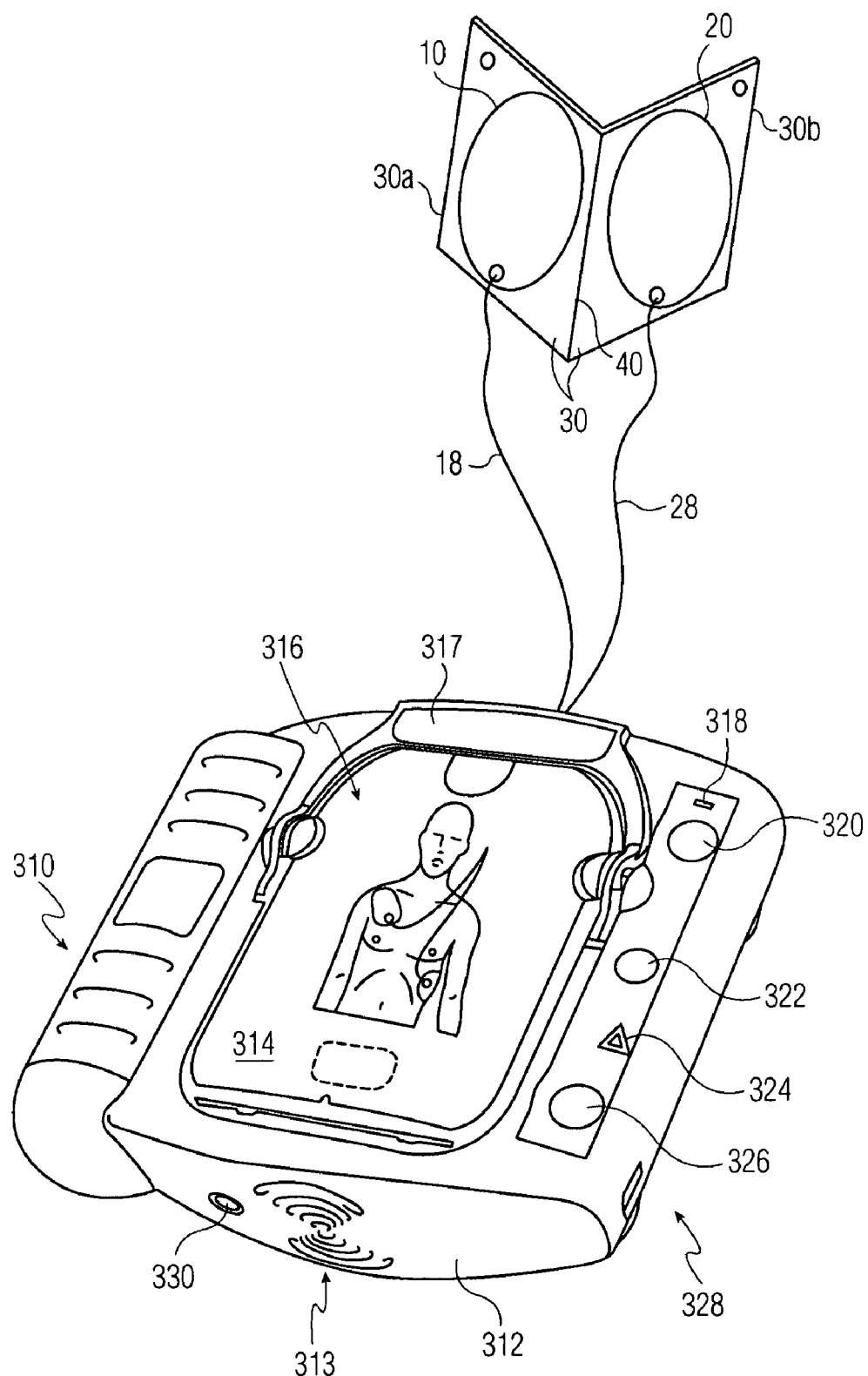
FIG. 4 illustrates a halibut-style release liner and electrodes connected to an AED.

FIG. 4 illustrates halibut electrodes of the present invention coupled to a defibrillator 310. The defibrillator 310 represents a semi-automatic external defibrillator (AED). However, other types of external defibrillators can be used as well. The AED 310 is housed in a rugged polymeric case 312 which protects the electronic circuitry inside the case, which was previously described with reference to FIG. 3, and also protects the rescuer from shocks. Attached to the case 312 by electrical leads 18,28 are a pair of halibut electrodes 10,20 attached to the two sides 30a,30b of a release liner 30. Prior to use the electrode pads 10,20 are retained in a cartridge 314 located in a recess on the top side of the AED 310. The electrode pads are accessed for use by pulling up on a handle 317 which allows removal of a plastic cover over the electrodes 10,20. The user interface is on the right side of the AED 310. A small ready light 318 informs the rescuer of the readiness of the AED 310. In this embodiment the ready light blinks after the AED 310 has been properly set up and is ready for use. The ready light is on constantly when the AED 310 is in use, and the ready light is off or flashes in an alerting color when the AED 310 needs attention.

Below the ready light is an on/off button 320. The on/off button is pressed to turn on the AED 310 for use. To turn off the AED 310 the rescuer holds the on/off button down for one second or more. An information button 322 flashes when information is available for the rescuer. The rescuer depresses the information button to access the available information. A caution light 324 blinks when the AED 310 is acquiring heartbeat information from the patient and lights continuously when a shock is advised, alerting the rescuer and others that no one should be touching the patient during these times. A shock button 326 is depressed to deliver a shock after the AED 310 informs the rescuer that a shock is advised. An infrared port 328 on the side of the AED 310 is used to transfer data between the AED 310 and a computer. This data port finds used after the patient has been rescued and a physician desires to have the AED 310 event data downloaded to his or her computer for detailed analysis. A speaker 313 provides voice instructions to the rescuer to guide the rescuer through the use of the AED 310 to treat the patient. A beeper 330 is provided which "chirps" when the AED 310 needs attention such as electrode pad replacement or a new battery.

Figure 5A:
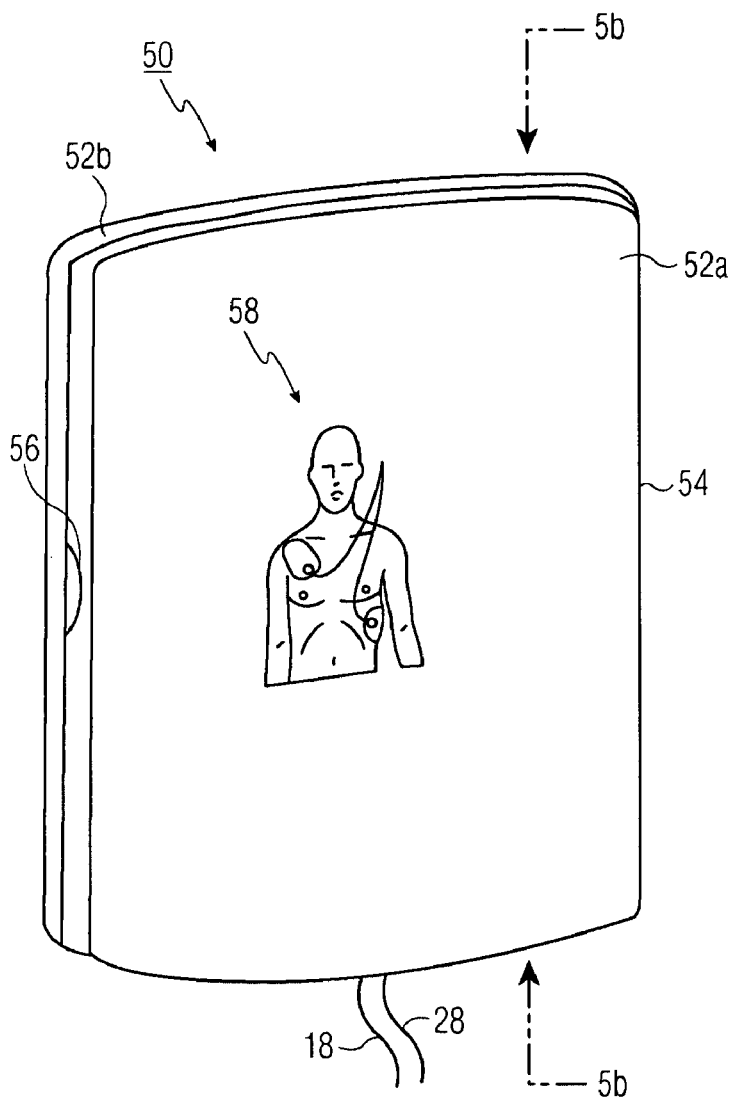
Figure 5B:
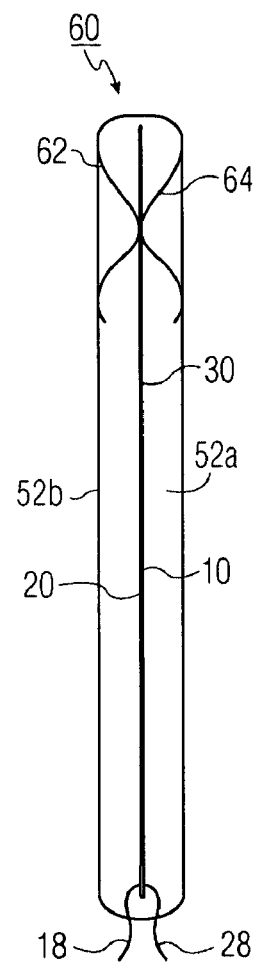

FIGS. 5a and 5b illustrate a case or cartridge 50 for storing halibut electrode pads prior to use in accordance with the principles of the present invention. The case 50 in this example is similar to the familiar cases which retain DVDs and can be made of a polymeric material, for instance. The two halves of the case 52a,52b are hinged together at one side by a hinge 54 and can be opened by depressing an indentation 56 on the other side of the case. While the case can be made to seal airtight as by the use of a gasket where the two halves come together or can be shrink-wrap sealed, this is not necessary as the peripheral sealing of the electrode pads 10,20 to a release liner 30 of polymeric or other moisture impermeable material will provide the necessary hermetic sealing of the electrode gel prior to use. A torso illustration 58 on the case illustrates the proper attachment of the electrodes to the patient.

The cross-sectional view of FIG. 5b shows that there is a spring clip 60 or other fastening device located inside the case. The two halves 62,64 of the spring clip are forced together when the case is closed, clamping the release liner 30 between them at the location of the holes 36,38. When the release liner is folded so that the two holes 36,38 oppose each other, this clamping action maintains contact of the two conductive sheets 44 of the release liner, completing the closed electrical circuit between the two electrode pads for self-test by a defibrillator attached to the electrical wires or leads 18,28. The case can also be used if the electrodes are not to be electrically connected by folding the release liner so that the holes are on the outside facing away from each other, in which case the clip 60 functions to retain the halibut electrodes and release liner in the case with no electrical connection between them. Thus, the same case 50 and halibut electrodes 10,20 and release liner 30 can be used for defibrillators which require and do not require electrical connection between the electrodes, simply by the way in which the release liner is folded inside the case.

Figure 6A:
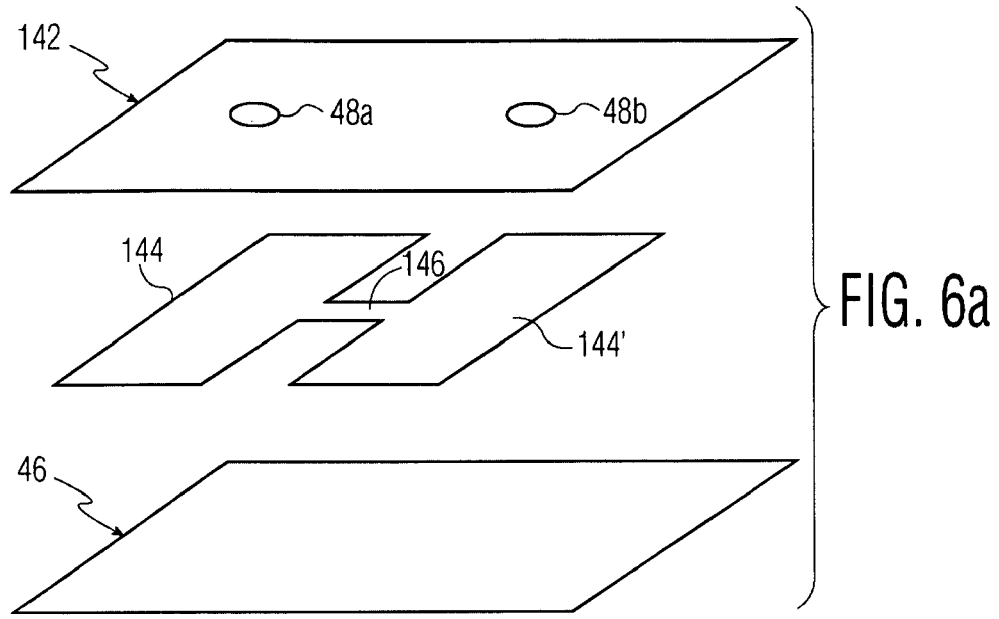
FIG. 6a illustrates a second example of a release liner of the present invention in an exploded view.
Figure 6B:
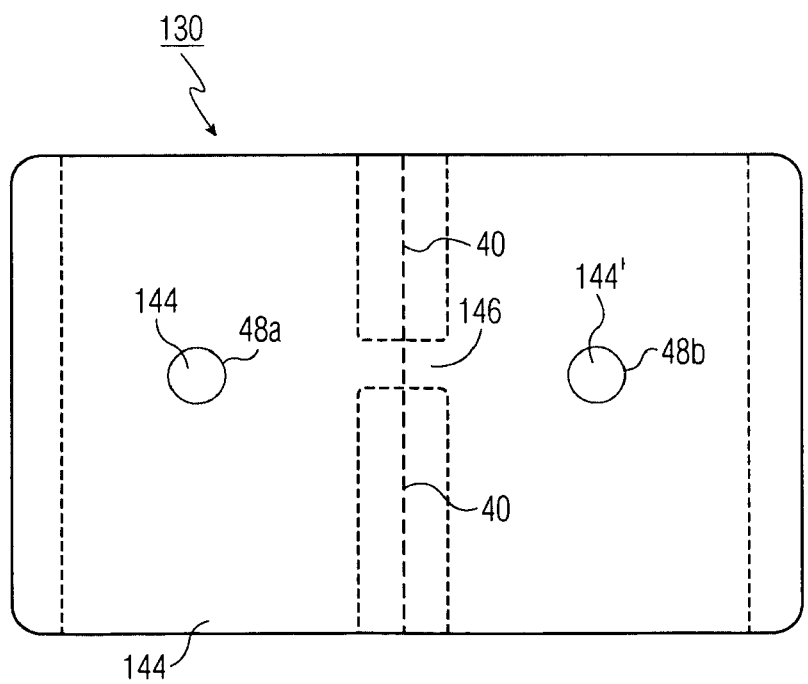
FIG. 6b is a plan view of the release liner of FIG. 6a after assembly and configured for a closed circuit connection to a defibrillator.

FIGS. 6a and 6b illustrate another example of a release liner for halibut electrodes of the present invention. In the exploded view of FIG. 6a the nonconductive release surface layer 142 of the release liner is seen to have only two holes, the holes 48a and 48b which underlie the electrodes when they are sealed to the layer 142 and permit electrical contact to an inner conductive sheet located between the outer nonconductive layers 142 and 46. The inner conductive sheet is composed of two sides 144 and 144' which underlie the holes 48a and 48b which are joined by a bridging portion 146. Thus the conductive sheet forms a continuous electrical connection between the two electrodes when they are attached to the release liner, as is evident from the plan view of the assembled release liner 130 of FIG. 6b. When the electrodes are attached to the surface 142 of the release liner 130 they are electrically connected to each other and ready for use with a defibrillator which requires electrically interconnected electrodes.

Figure 7A:
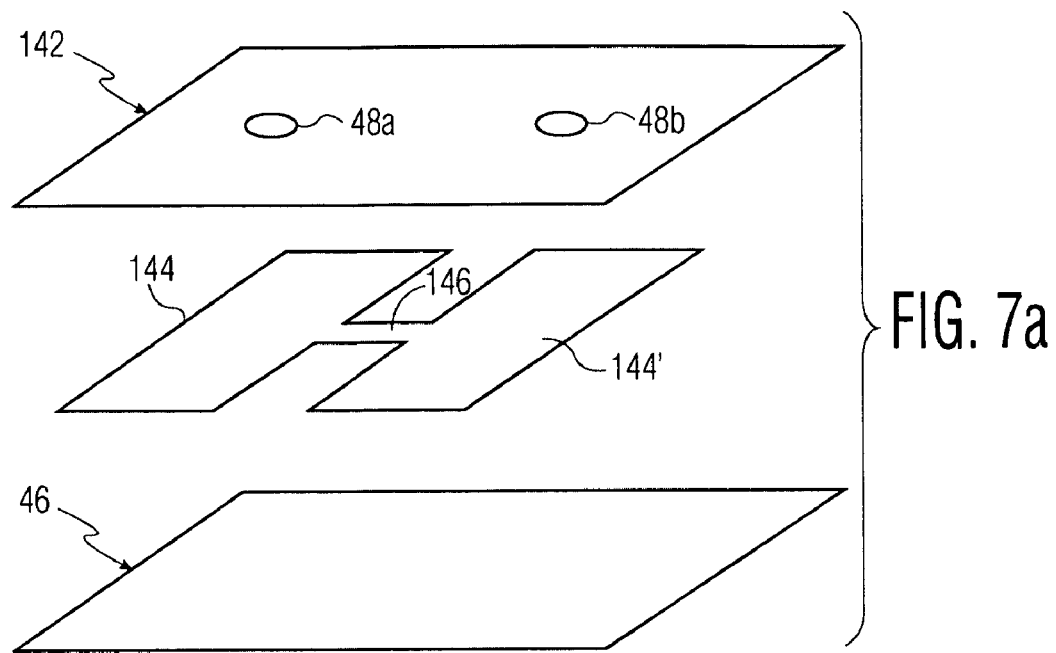
FIG. 7a illustrates the second example of a release liner of the present invention in an exploded view.
Figure 7B:
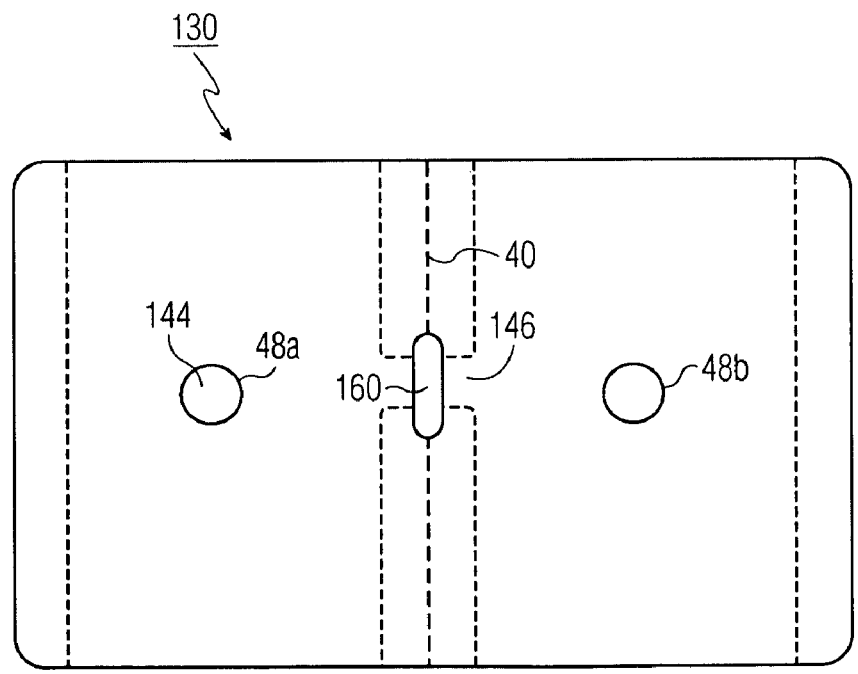
FIG. 7b is a plan view of the release liner of FIG. 7a after assembly and configured for an open circuit connection to a defibrillator.

The release liner configuration of FIGS. 6a and 6b can be converted to one in which the attached electrodes are not electrically interconnected as shown in FIGS. 7a and 7b. This is done by breaking the electrical connection between the two sides of the release liner 130. In the example of FIG. 7b this is done by punching a hole 160 through the release liner which severs the bridging portion 146 between the two halves 144 and 144' of the inner conductive sheet. The two halves 144 and 144' of the conductive sheet are thus no longer electrically connected to each other. Unlike the embodiment of FIGS. 1, 2a and 2b, the electrical interconnection or lack thereof is not determined by the manner in which the release liner is folded; it is determined by whether the two halves of the conductive sheet remain connected or are disconnected. The example of FIGS. 6a, 6b, 7a and 7b can be folded or unfolded in either configuration. Also unlike the earlier embodiment, the severing of the two halves of the conductive sheet make the non-interconnected configuration permanent, absent means to reconnect the two halves of the conductive sheet. Another way to view the two embodiments is that the two halves of the conductive sheet are nominally not connected in the FIGS. 1, 2a, 2b embodiment and nominally electrically connected in the FIGS. 6a, 6b, 7a, 7b embodiment. Breaking the electrical connection of the latter changes the configuration to use defibrillators requiring non-connected electrodes. For example, at the end of the manufacturing process the two halves of the conductive sheet can be left connected and the halibut electrodes used with defibrillators requiring electrically connected electrodes, or the bridging portion 146 can be cut and the halibut electrodes used with defibrillators requiring electrically disconnected electrodes. The same electrode manufacturing line can thus make electrodes for both types of defibrillators.

Figure 8A:
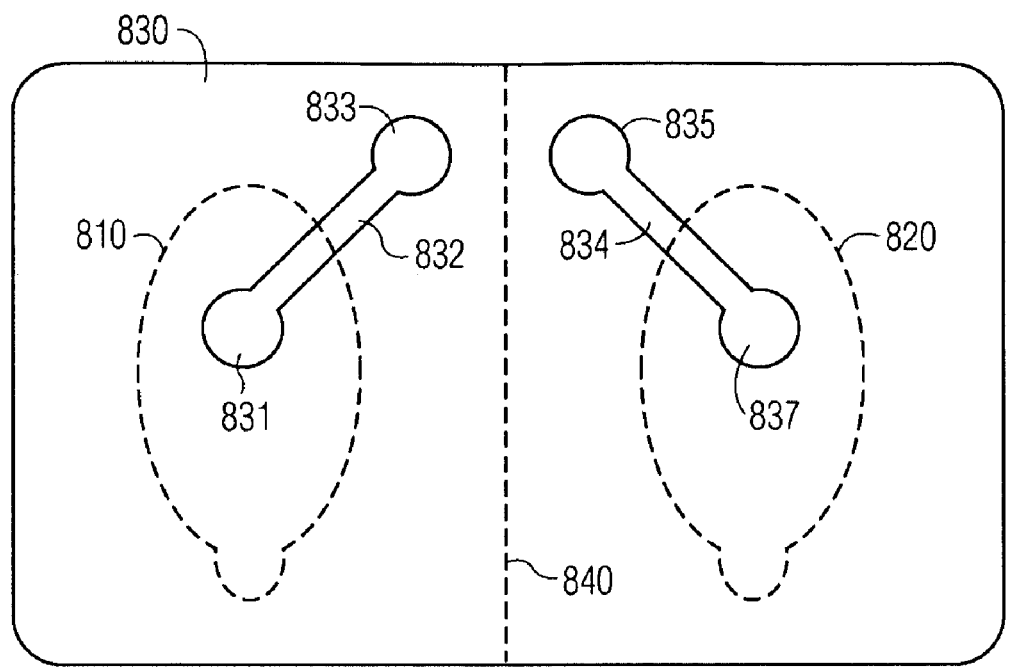
FIG. 8a is a plan view of a halibut release liner which is folded to electrically connect the electrodes and uses a single release liner sheet.

FIG. 8a is another example of a halibut release liner of the present invention. In this example the release liner comprises a single sheet 830 of moisture impermeable material to which electrodes are attached as above with the conductive gel facing the sheet. When the electrodes are peripherally sealed to the release liner sheet 830 the conductive gel of the electrodes is sealed as before between the moisture impermeable backing of the electrode and the moisture impermeable release liner sheet 830, protecting the gel from desiccation. Dashed lines 810 and 820 indicate the areas of the release liner where the electrodes are to be attached. The release liner sheet 830 may be formed of a polymeric or plastic material or other material that is nonconductive. Conductors 832 and 834 formed of thin foil, metallized ink, or other thin conductor is laminated or printed on the sheet with a portion of each positioned to contact the electrically conductive (gel) surface of the electrode and another portion extending outside of the attachment areas of the electrodes. In this example the conductors each have one rounded end 831,837 which makes contact with the conductive gel of an attached electrode and another rounded end 833,835 outside of the attachment areas 810,820. In this example the conductors 832,834 are laminated or printed on the side of the sheet 830 where the electrodes are to be attached, but they could also be located on the opposite side of the sheet 830 and make electrical contact through holes in the sheet. The conductors could also be embedded or molded into the sheet 830. The electrodes can be attached on the same side or on opposite sides of the sheet 830.

When the electrodes are attached in the electrode attachment areas 810 and 820, each attached electrode will be in electrical contact with a respective one of the conductors 832 and 834. When the sheet 840 is folded along fold line 840 so that conductor ends 833 and 835 are brought into contact with each other, the electrodes will be electrically connected to each other for a defibrillator which requires electrically connected electrodes for self-test. But when the sheet is folded the other way or left unfolded so that there is no electrical contact between conductors 832 and 834, the electrodes and release liner are suitable for connection to a defibrillator which does not require or cannot have preconnected electrodes electrically connected to each other.

The release liner sheet 830 can be opaque, translucent, or transparent. A transparent sheet will enable a user to visually inspect the conductive gel of the electrodes through the sheet 830 while the electrodes are attached to the release liner to discern any deterioration of the gel. The gel may contain a substance or material which changes color or otherwise changes visually when the moisture content of the gel changes, providing a quick and easy means for determining whether the electrodes are suitable for use.

Figure 8B:
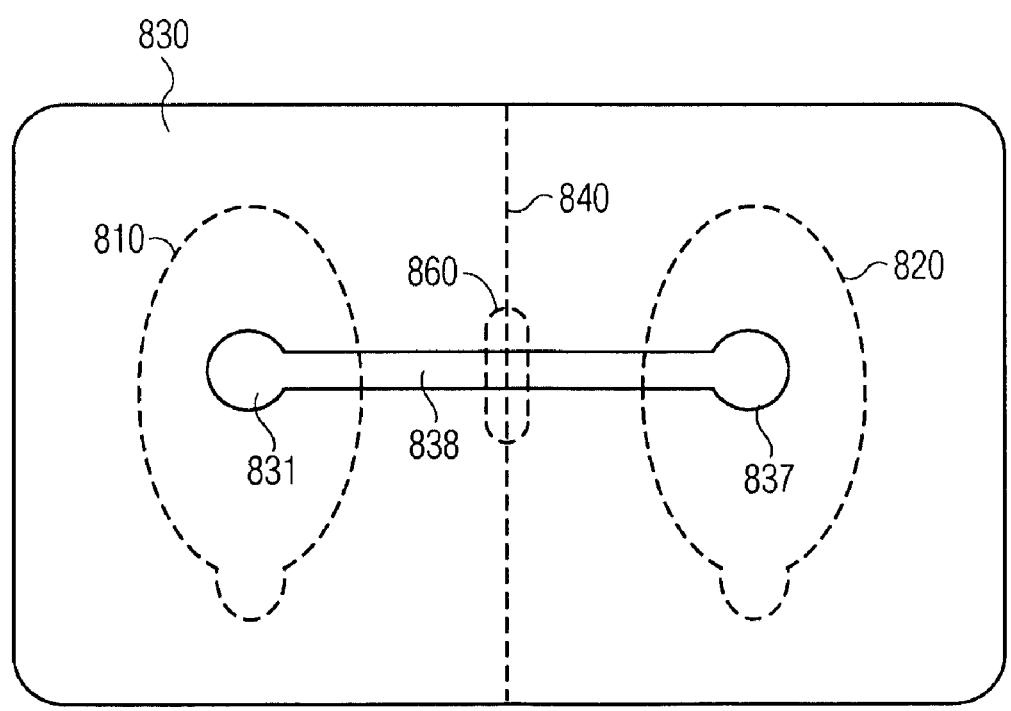
FIG. 8b is a plan view of a halibut release liner which is punched or cut to electrically disconnect the electrodes and uses a single release liner sheet.

FIG. 8*b* is another example of the present invention which, as in the example of FIG. 8*a*, uses a single release liner sheet 830. Instead of separate conductors, a conductor 838 is laminated to, printed on, or embedded in the sheet 830 and extends between the attachment position 810 for one electrode and the attachment position 820 for the other electrode. As before, the conductor 838 is preferably on the same side of the sheet 830 to which the electrodes are attached, but could also be on the other side and extend through the sheet to the two electrodes. When electrodes are attached to the release liner sheet 830 in the positions shown, the electrodes are electrically connected to each other by the conductor 838. If the conductor 838 is broken such as by punching a hole 860 through the conductor or through the conductor and the release liner sheet, the attached electrodes are rendered electrically disconnected with each other.

Other variations will readily occur to those skilled in the art. For instance, the conductors for the example of FIG. 8*a* could simply comprise small conductors at the locations and of the size of ends 831 and 837 with holes in sheet 830 behind the conductors providing access to conductors 831 and 837 on the back of sheet 830. When the release liner sheet 830 is folded back-to-back, the conductors 831 and 837 can be brought into contact with each other through the holes in the sheet 830 and clamped or attached into continuous contact to electrically connect the two electrodes. Folding the sheet the opposite way or leaving the sheet unfolded would leave the electrodes electrically disconnected with each other. Other variations of the examples described above are also possible.

The clip 150 of FIG. 2*b* can be used to retain the release liner of FIG. 8*a* in its desired folded configuration, either with the two electrodes electrically connected or folded with the two electrodes electrically separated. Likewise the case of FIGS. 5*a* and 5*b* can be used to protect and retain the release liner of FIG. 8*a* in either folded configuration. For the variation described in the previous paragraph which only has small conductors 831,837 located under the electrodes and accessible at the back of the release liner 830 through holes in the release liner sheet, the spring clip 60 or other retention device inside the case will be aligned with the conductors 831,837 so that the desired electrical contact through the holes of the release liner sheet is maintained by contact of the conductors 831 and 837.

What is claimed is:

1. A release liner for electrodes which may be selectively configured to electrically connect electrodes attached to the release liner comprising:
    an outer nonconductive surface to which electrodes may be attached;
    a conductive layer in electrical contact with each attached electrode and nominally electrically disconnected with each other; and
    an access to the conductive layer of each attached electrode; and
    an attachment device which can be applied to the release liner when the release liner is folded with the accesses to the conductive layers in alignment,
    wherein the release liner may be folded one way and the attachment device applied to bring the conductive layer of each attached electrode into electrical connection, or folded another way to leave the conductive layer of each attached electrode in electrical disconnection.

2. The release liner of claim 1, wherein the attachment device comprises a clamping device.

3. The release liner of claim 1, wherein the attachment device comprises a conductive adhesive.

4. The release liner of claim 1, wherein the access comprises a hole through the outer nonconductive surface.

5. The release liner of claim 1, further comprising a second outer nonconductive surface,
    wherein the conductive layer is sandwiched between the first and second nonconductive surfaces.

6. The release liner of claim 5, wherein the conductive layer further comprises first and second inner conductive layers.

7. The release liner of claim 1, wherein the nonconductive surface is impermeable to moisture.

8. The release liner of claim 1, wherein the attachment device is located in a case which can be opened and closed and which encloses the release liner and electrodes prior to use,
    wherein closing the case causes the attachment device to clamp the conductive layer of each electrode into electrical contact when the release liner is folded the one way.

9. The release liner of claim 1, wherein the attachment device is located in a case which can be opened and closed and which encloses the release liner and electrodes prior to use,
    wherein closing the case causes the attachment device to clamp the release liner with the attachment device without electrical connection between the two electrodes when the release liner is folded the another way.

10. The release liner of claim 8, wherein the case is made of a rigid polymeric material.

11. The release liner of claim 9, wherein the case is made of a rigid polymeric material.

12. A release liner for electrodes which may be selectively configured to electrically connect electrodes attached to the release liner comprising:
- an outer nonconductive surface to which the electrodes are attached;
- a conductor in electrical contact with each attached electrode and nominally electrically disconnected from each other; and
- a case including two covers which may be opened and closed which encloses the release liner and electrodes prior to use, each cover including a portion of a retaining device which, when the case is closed, retains the release liner,
- wherein when the release liner is folded one way the retaining device retains the electrodes in the case in an electrically connected configuration, and when the release liner is not folded the one way the retaining device retains the electrodes in the case in an electrically disconnected configuration.

13. The release liner of claim 12, wherein the conductors in electrical contact with each attached electrode are in opposition and in contact with each other when the release liner is folded the one way.

14. The release liner of claim 13, wherein the retaining device comprises a spring clip.

15. The release liner of claim 12, wherein the retaining device is located at the center of the cover.

16. The release liner of claim 12, wherein the retaining device clamps the release liner when the case is closed without the electrodes being located in the retaining device.

17. A method for packaging a pair of electrodes attached to a release liner, the release liner including a conductor electrically connected to the electrically conductive surface of each electrode, comprising:
- folding the release liner one way which brings the conductors into opposition with each other, or folding the release liner another way which does not bring the conductors into opposition with each other; and
- placing the release liner and electrodes in a case having covers which may be closed to enclose the release liner and electrodes, each cover including a portion of a retaining device which retains the release liner in the retaining device when the cover is closed,
- wherein the retaining device retains the conductors in electrical contact with each other when the release liner is folded the one way.

18. The method of claim 17, wherein the retaining device retains the release liner with the conductors not in electrical contact with each other when the release liner is folded the another way.

* * * * *